(12) United States Patent
Suonpää et al.

(10) Patent No.: US 12,215,119 B2
(45) Date of Patent: Feb. 4, 2025

(54) METHOD FOR OBTAINING LOW MOLECULAR WEIGHT LIGNIN

(71) Applicant: METGEN OY, Kaarina (FI)

(72) Inventors: Anu Minna Maaret Suonpää, Kaarina (FI); Matti Wilhelm Heikkilä, Kaarina (FI); Joana Raquel Amaral Antunes, Kaarina (FI); Klara Birikh, Kaarina (FI)

(73) Assignee: Metgen OY, Kaarina (FI)

( * ) Notice: Subject to any disclaimer, the term of this patent is extended or adjusted under 35 U.S.C. 154(b) by 805 days.

(21) Appl. No.: 17/420,921

(22) PCT Filed: Jan. 3, 2020

(86) PCT No.: PCT/EP2020/050089
§ 371 (c)(1),
(2) Date: Jul. 6, 2021

(87) PCT Pub. No.: WO2020/144115
PCT Pub. Date: Jul. 16, 2020

(65) Prior Publication Data
US 2022/0064200 A1    Mar. 3, 2022

(30) Foreign Application Priority Data
Jan. 7, 2019 (EP) .................................... 19150546

(51) Int. Cl.
*C07G 1/00* (2011.01)
*C08J 11/10* (2006.01)

(52) U.S. Cl.
CPC ................. *C07G 1/00* (2013.01); *C08J 11/10* (2013.01)

(58) Field of Classification Search
CPC .................................. C07G 1/00; C08J 11/10
USPC ......................................................... 530/500
See application file for complete search history.

(56) References Cited

FOREIGN PATENT DOCUMENTS

| WO | 2017102540 A1 | 6/2017 | |
|---|---|---|---|
| WO | WO-2017102523 A1 * | 6/2017 | ............. C12N 15/63 |
| WO | 2018019707 A1 | 2/2018 | |
| WO | WO-2018226147 A1 * | 12/2018 | ............ B01J 23/882 |

OTHER PUBLICATIONS

Hamalainen, Veera et al., "Enzymatic Processes to Unlock the Lignin Value." Frontiers in Bioengineering and Biotechnology, vol. 6: Mar. 22, 2018, pp. 1-10.

Lew, Paul Christopher et al., "Lignin Biodegradation with Laccase-Mediator Systems", Frontier in Energy Research, vol. 2, Article 12, Mar. 31, 2014, pp. 1-13.

(Continued)

*Primary Examiner* — David T Karst
(74) *Attorney, Agent, or Firm* — Patent Law Works LLP (57) ABSTRACT

The invention relates to obtaining lignin preparations of desirable molecular size and properties. It describes a method of de-polymerizing lignin of high molecular weight into low molecular weight lignin. More in particular, the invention provides a method for producing lignin with a low molecular weight wherein high molecular weight lignin is contacted with an alkaline laccase at alkaline pH in a reaction vessel and wherein the lignin with a molecular weight below 2 kDa is selectively removed from the reaction vessel during the reaction.

11 Claims, 5 Drawing Sheets
Specification includes a Sequence Listing.

(56) References Cited

OTHER PUBLICATIONS

PCT International Search Report and Written Opinion; Application No. PCT/EP2020/050089, international filing date of Jan. 3, 2020 Metgen Oy, date of mailing Feb. 12, 2020, 11 pages.

Munk, Line, et al. Can laccases catalyze bond cleavage in lignin, Biotechnology Advances (2015), doi: 10.1016/j.biotechadv.2014.12.008, 47 pgs.

Canas, Ana I., and Susana Camarero. "Laccases and Their Natural Mediators: Biotechnological Tools for Sustainable Eco-Friendly Processes." Biotechnology Advances, vol. 28, No. 6, 2010, pp. 694-705.

Yao, Bin, et al. "Laccase-Natural Mediator Systems for "Green" Synthesis of Phenolic Monomers from Alkali Lignin." Sustainable Energy Fuels, vol. 1, No. 7, 2017, pp. 1573-1579.

\* cited by examiner

METHOD FOR OBTAINING LOW MOLECULAR WEIGHT LIGNIN

CROSS REFERENCE TO RELATED APPLICATIONS

This application is a national phase entry under 35 U.S.C. § 371 of International Patent Application PCT/EP2020/050089, filed Jan. 3, 2020, designating the United States of America and published in English as International Patent Publication WO 2020/144115 on Jul. 16, 2020, which claims the benefit under Article 8 of the Patent Cooperation Treaty to European Patent Application Serial No. 19150546.0, filed Jan. 7, 2019, the entireties of which are hereby incorporated by reference.

FIELD OF THE INVENTION

The invention relates to obtaining lignin preparations of desirable molecular size and properties. It describes a method of de-polymerizing lignin of high molecular weight into low molecular weight lignin.

BACKGROUND OF THE INVENTION

Lignin (CAS Number 9005-53-2) is a class of complex organic polymers that form key structural materials in the support tissues of vascular plants and some algae [1]. Lignins are particularly important in the formation of cell walls, especially in wood and bark, because they lend rigidity and do not rot easily. Chemically, lignins are cross-linked phenolic polymers [2].

As a biopolymer, lignin is unusual because of its heterogeneity and lack of a defined primary structure. Its most commonly noted function is the support through strengthening of wood (mainly composed of xylem cells and lignified sclerenchyma fibers) in vascular plants [3].

Lignin is a cross-linked polymer with a very divers size distribution, wherein the largest molecules have a molecular weight in excess of 100,000 Dalton (Da). It is relatively hydrophobic and rich in aromatic subunits. The degree of polymerzation is difficult to measure, since the material is very heterogeneous. Different types of lignin have been described depending on the means of isolation.

Figure 1:
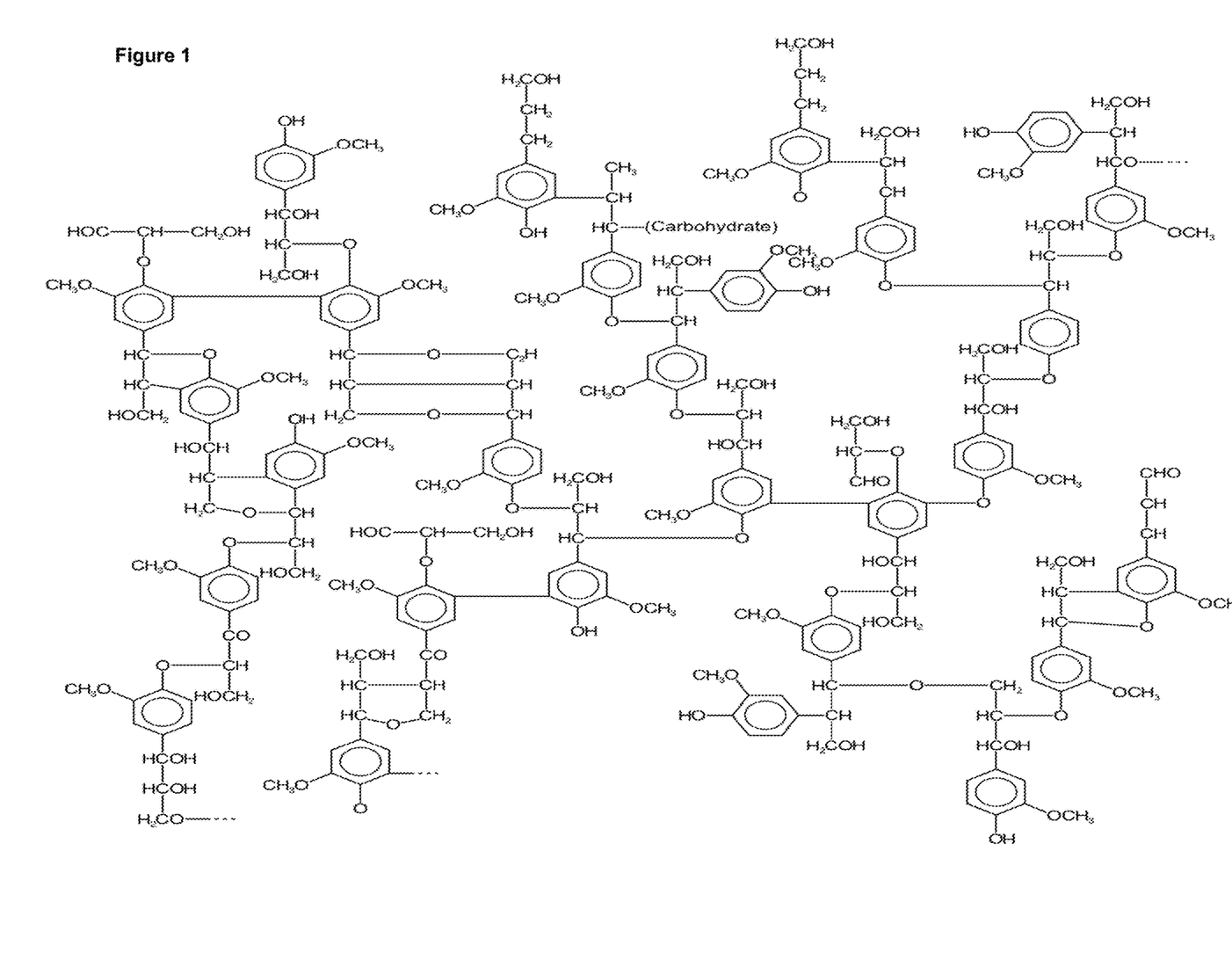
FIG. 1: An example of a lignin structure [10].

The lignols (monomers incorporated in lignin) that crosslink are of three main types, all derived from phenylpropane: 4-hydroxy-3-methoxyphenylpropane, 3,5-dimethoxy-4-hydroxyphenylpropane, and 4-hydroxyphenylpropane. The former tends to be more prevalent in conifers and the latter in hardwoods. An example of a possible lignin structure is shown in FIG. 1.

Three monolignol monomers (FIG. 2) are precursors, all of which are methoxylated to various degrees: p-coumaryl alcohol, coniferyl alcohol, and sinapyl alcohol [4]. These lignols are incorporated into lignin in the form of the phenylpropanoids p-hydroxyphenyl (H), guaiacyl (G), and syringyl(S), respectively [5]. Gymnosperms have a lignin that consists almost entirely of G with small quantities of H. That of dicotyledonous angiosperms is more often than not a mixture of G and S (with very little H), and monocotyledonous lignin is a mixture of all three [5]. Many grasses have mostly G, while some palms have mainly S [6]. All lignins contain small amounts of incomplete or modified monolignols, and other monomers are prominent in non-woody plants [7].

In order to achieve desirable properties for industrial applications, lignin needs to be fragmented to a lower molecular weight. This process is often referred to as de-polymerization. However, in contrast to other bio-polymers (e.g. proteins, DNA, and even cellulose), lignin is resistant to degradation and acid- and base-catalyzed hydrolysis. In spite of their heterogeneous character, many, if not all lignins, were found to be susceptible to enzymatic degradation and a large number of enzymatic processes for the degradation of lignin have been described. Some ligninolytic enzymes include heme peroxidases such as lignin peroxidases, manganese peroxidases, versatile peroxidases, and dye-decolourizing peroxidases as well as copper-based laccases.

Enzymatic modification of lignin has been recognized as an important aspect of the successful refining of lignocellulosic biomass, and enzyme-assisted processing of lignin received significant attention in the literature.

Laccases (EC 1.10.3.2) are taking the center stage of this attention, since these enzymes may help degrading lignin, using oxygen as the oxidant. Laccase-mediator systems have been implicated as the most promising tool addressing lignin recalcitrance. Mediators are small molecules, which act as electron shuttles, providing the oxidation of complex substrates such as lignin polymers. Once oxidized by the enzyme and stabilized in more or less stable radicals, mediators diffuse far away from the enzymatic pocket and, by mechanisms different from the enzymatic one, enable the oxidation of target compounds that in principle are not substrates of laccase because of their large size or high redox potential.

Laccases can catalyze polymerization of lignin, but recently they have been described to directly catalyze modification of lignin via catalytic bond cleavage [8]. Therein it was described that laccases are able to catalyze bond cleavage in low molecular weight phenolic lignin model compounds, however, it was found that a mediator system was required for the laccases to catalyze inter-unit bond cleavage in natural lignin substrates. In the absence of a mediator, laccases were found to contribute to the polymerization of lignin [8].

Hence, there remains a need in the art for a process on an industrial scale for the production of low molecular weight lignin.

SUMMARY OF THE INVENTION

The invention relates to a method for producing lignin with a low molecular weight wherein high molecular weight lignin is contacted with an alkaline laccase at alkaline pH in a reaction vessel and wherein the lignin with a molecular weight below 2 kDa is selectively removed from the reaction vessel during the reaction

DETAILED DESCRIPTION OF THE INVENTION

We recently described a process wherein lignin was treated with a bacterial laccase at alkaline pH. We herein repeated the experiments described in Hamalainen [9] and confirmed that incubation of lignin with an alkaline laccase after one hour of incubation resulted in de-polymerization of lignin; i.e. the fraction of higher molecular weight lignin molecules decreased and the fraction of lower molecular weight increased. This is shown in FIG. 1. Notably, when the reaction mixture was analyzed after one hour of incubation by size-exclusion chromatography, we found that two peaks of low molecular weight species had appeared (about 180 Da and 360 Da, FIG. 3, arrows). This molecular weight coincides with the molecular weight of lignin monomers and dimers. Hence, we confirmed that alkaline laccase was capable of depolymerizing lignin, i.e. converting high molecular weight lignin to low molecular weight lignin.

As used herein, the term "high molecular weight lignin" indicates lignin with a molecular weight above 2 kDa, such as above 5 kDa, 10 kDa, 20 kDa or even 50 kDa. For practical purposes, it is preferred when the high molecular weight lignin has a molecular weight below 100 kDa, such as 80 kDa, 70 kDa or 60 kDa.

Conversely, the term "low molecular weight lignin" is used herein to indicate a lignin with a molecular weight below 2 kDa, preferably below 1 kDa, such as 900 Da, 800 Da, 700 Da, 600 Da, 500 Da, 400 Da, 300 Da, or even 200 Da.

The term "polymerization" as used herein is meant to refer to a process wherein the molecular weight of a lignin molecule increases. This may be caused by covalently coupling monomers to an already existing polymer or oligomer, it may also be attributable to polymers or oligomers covalently coupling to each other. Polymerization may therefore refer to a process which results in an increase of high molecular weight species of lignin and a decrease of low molecular weight species of lignin.

The term "de-polymerization" as used herein is meant to refer to a process wherein the molecular weight of a lignin molecule decreases. This may be caused by opening covalent bonds between monomers, oligomers and polymers or between polymers and oligomers. De-polymerization may therefore refer to a process which results in an increase of low molecular weight species of lignin and a decrease of high molecular weight species of lignin.

The term "oligomer" is used to refer to a molecule that consists of between 2 and 10 lignin monomers (lignols). Polymers consist of 10 or more lignols.

The term "alkaline laccase" as used herein refers to a laccase enzyme (E.C. 1.10.3.2) that is able to oxidize its substrate, such as phenolic compounds, such as lignin, at a pH above 7.

In the above described experiment (FIG. 3, t=1 h), the yield of low molecular weight lignin was rather low. In order to increase that yield, we let the reaction continue for 5 hours instead of 1 hour, stopped the reaction and analyzed the reaction products again by size-exclusion chromatography. Surprisingly, instead of further increasing the low molecular weight lignin fraction, this resulted in polymerization of lignin, i.e. a decrease of the low molecular weight lignin fraction and in an increase of the high molecular weight fraction. The two peaks at 180 and 360 Da decreased, whereas we observed a significant increase in material with a molecular weight between 10 and 100 kDa (FIG. 1, t=5 h).

Figure 2:
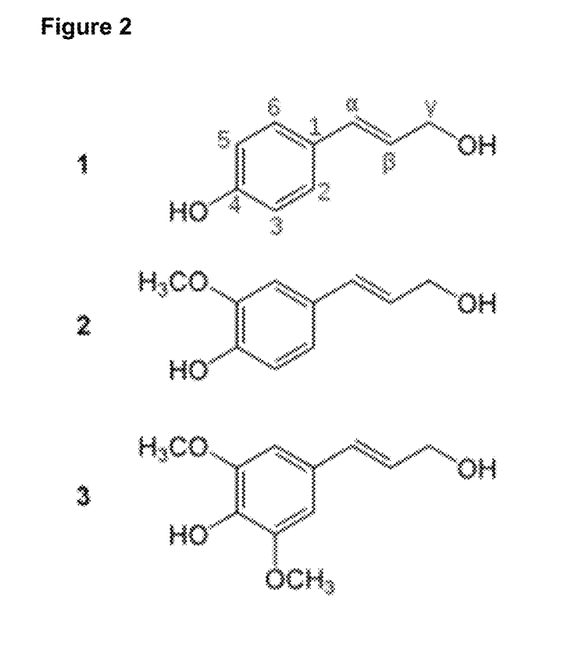
FIG. 2: The three common monolignols: paracoumaryl alcohol (1), coniferyl alcohol (2) and sinapyl alcohol (3)

Even more surprising, we were able to reach the goal of increasing the yield of low molecular weight lignin by removing the low molecular weight lignin from the reaction vessel during the reaction. In particular, the removal of low molecular weight lignin with a molecular weight below 2 kDa using ultrafiltration with a filter with a molecular cut-off of 2 kDa proved to be very effective. It resulted in a sharp increase of the yield of low molecular weight lignin and at the same time it prevented the formation of high molecular weight lignin in the retentate in the reaction vessel (FIG. 2).

This phenomenon is particularly unexpected as the prior art teaches that monomers of lignin can serve as mediators in lignin oxidation and thus are known to promote depolymerization [8].

Hence, the invention relates to a method for producing lignin with a low molecular weight wherein high molecular weight lignin is contacted with a laccase at alkaline pH in a reaction vessel and wherein the lignin with a molecular weight below 2 kDa is selectively removed from the reaction vessel during the reaction.

The term "alkaline pH" is used herein to indicate a pH above 7, preferably above 8, such as 9, 10, 11, 12 or 13. In a further preferred embodiment, the pH is at or around the optimum pH for lignin oxidation with the laccase used, such as between 7 and 14, such as between 8 and 12 or 13, such as between 9 and 11 or 12, preferably at about 10 or 10.5.

The phrase "selectively removed" is used herein to indicate that the fraction of lignin molecules with a low molecular weight is removed from the reaction mixture to a larger extent than at least some of the lignin molecules with a higher molecular weight.

The phrase "selectively removed from the reaction vessel during the reaction" relates to a method wherein the reaction between the laccase and the lignin is ongoing, while (part of) the low molecular weight lignin fraction is removed from the reaction vessel. The skilled person is familiar with techniques how this may be achieved, such as for example by ultrafiltration in a fed-batch reactor or a continuous flow reactor.

The lignin used in the examples had an average molecular weight between 5 and 11 kDa. The teachings described herein should not be interpreted so narrowly that the method can only be performed with lignin of that particular size. We obtained comparable results with lignin of an average molecular weight of between 10 and 30, between 40 and 60, and between 80 and 100 kDa. It was observed that the appearance of high molecular species (polymerization) was prevented when the lignin fraction with a molecular weight below 2 kDa was removed from the reaction mixture while the reaction was ongoing.

The laccase enzyme used in the experiments described in the examples section is a known enzyme (WO 2018/019707) obtained from B. wakoensis (SEQ ID NO: 1). The teaching as provided herein should not be so narrowly construed as that it relates only to the exemplified sequence of SEQ ID NO: 1. It is well known in the art that protein sequences may be altered or optimized, for instance by site-directed mutagenesis, in order to arrive at proteins with identical or even improved properties. The closest known protein to the B. wakoensis laccase is a protein with 64% sequence identity. Hence, the invention relates to a method as described herein, wherein the laccase has an amino acid sequence at least 90% identical to SEQ ID NO: 1. The term "at least 90%", is to be interpreted as 90%, 91, 92, 93, 94, 95, 96, 97, 98, 99 or more %.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2s eq&LINK_LOC=align2seq, Other commercial and open software such as Vector NTI are also suitable for this purpose.

The invention may also be described in different terms. Without wanting to be bound by theory, we speculate that the monomers and dimers that are generated in the laccase-catalyzed reaction, trigger the polymerization of low and high molecular weight lignin, thereby generating molecules with a higher molecular weight than the starting material. This polymerization reaction then overtakes the de-polymerization reaction and favors the generation of higher molecular weight species. This may then be prevented by depleting the reaction of such monomers and dimers, for instance by removing the lignin fraction with a molecular weight below 2 kDa from the reaction mixture while the reaction is ongoing. The phrase "removing the lignin fraction with a molecular weight below 2 kDa" or equivalent refers to the depletion of the reaction mixture from lignin species smaller than 2 kDa, such as smaller than 1 kDa, 900 Da, 800 Da, 700 Da, 600 Da, 500 Da, or even smaller than 400 Da. The invention therefore also refers to a method wherein the reaction mixture for example is depleted of lignin molecules smaller than 1 kDa, such as a 900 Da, 800 Da, 700 Da, 600 Da, 500 Da, or even smaller than 400 Da.

This may be achieved by ultrafiltration with a filter with a molecular cut-off of 2 kDa, such as a molecular cut-off of 1 kDa, such as 900 Da, 800 Da, 700 Da, 600 Da, 500 Da, or even smaller than 400 Da. In an alternative embodiment of the invention, the advantageous effect of the invention may also be achieved by ultrafiltration with a filter with a cut-off value larger than 2 kDa, such as 3, 4, 5, 6, 7, 8, 9, or 10 kDa, such as larger than 20, 30, 40, 50, 60 or 70 kDa or larger, as long as the low molecular weight fraction of lignin is selectively removed from the reaction mixture.

"Depletion" refers to the act of decreasing the relative amount of the lignin species smaller than 2 kDa. In no way this term is to be interpreted to mean that a particular fraction should be entirely or quantitatively be removed. It is sufficient to reduce the amount of the fraction concerned (in this case at least part of the low molecular weight fraction) in order to obtain the desired effect.

The invention may also be described in yet different terms. In one embodiment, the invention relates to a method for enzymatically depolymerizing lignin wherein the lignin is reacted with a laccase at alkaline pH at a temperature suitable for the laccase to depolymerize the lignin in a reaction vessel, wherein low molecular weight lignin is removed from the reaction vessel during the course of the reaction.

In yet other terms, the invention relates to a method for enzymatically polymerizing and de-polymerizing lignin wherein lignin is contacted with an alkaline laccase in a reaction vessel at alkaline pH, wherein the equilibrium between polymerization and de-polymerization is shifted towards de-polymerization by removing low molecular weight fractions of lignin from the reaction vessel during the enzymatic oxidation reaction, wherein the low molecular weight lignin has a molecular weight below 2 kDa.

The term "average molecular weight" of a population of molecules as used herein refers to a molecular weight wherein the total mass of the molecules with a molecular weight that is higher than the average molecular weight is equal to the total mass of the molecules with a molecular weight that is lower than the average molecular weight.

Average molecular weight of a population of lignin molecules can be determined by size exclusion chromatography profiles as described in Example 5. Relative mass of a sub-population of molecules can be determined by integration of HPLC peaks corresponding to the sub-population and dividing by the total integral of the population profile.

EXAMPLES

Example 1: HPLC, Enzyme Activity Measurement

Specific enzyme activity the laccase according to SEQ ID NO: 1 [9] was determined using ABTS as a substrate. Reaction mixture was prepared by mixing 20 ul of diluted enzyme with 430 microliter of 100 mM Sodium Acetate pH 4.5 in 1-cm-light-path spectrophotometer cuvette, the mixture was equilibrated to 60 degrees Celsius (C); the reaction was initiated by adding 50 ul of ABTS solution and incubated at 60 C. UV measurements at 405 nM were performed every 2 min. One unit of laccase activity was defined as the amount of enzyme oxidizing 1 micro mole of ABTS per minute under these conditions, wherein the extinction coefficient of ABTS at 405 nm is 36800 M-1 cm-1). Enzyme activity is herein also expressed as katals, wherein one microkatal is the amount of enzyme oxidizing 1 micromole of substrate per second, hence 1 microkatal equals 60 units.

Example 2: Preparation of alkali-soluble lignin

Figure 3:
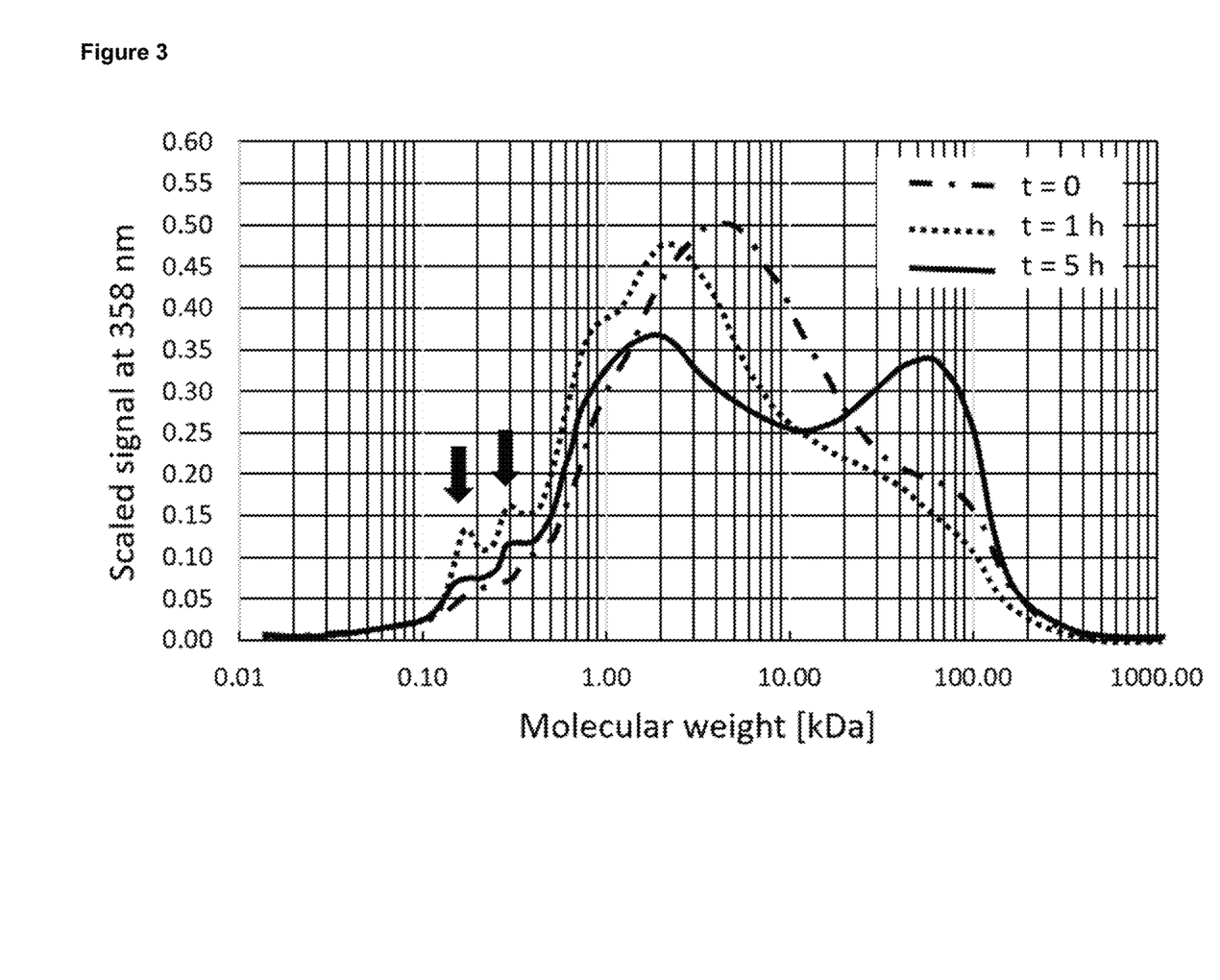
FIG. 3: Molecular weight distribution of lignin molecules determined by size exclusion chromatography in a batch mode reaction according to the prior art [9] after reaction time t. Dash-dotted line: starting point t=0; dotted line: t=1 h; solid line: t=5 h. Arrows show approximate molecular weights of monomer and dimer lignin units.

Hardwood lignin was obtained from an industrial source (Sweetwater Inc.). Alkali-soluble lignin was prepared as follows: Hardwood lignin was solubilized at 100 g/l in 0.25 M NaOH, mixed for 30 minutes at room temperature, centrifuged at 6000 g for 20 minutes and the supernatant was dried in oven at 105 C and stored at room temperature until used. The dried alkaline-soluble lignin was then dissolved to completion at 25 g/l in water and pH adjusted to 10.5. The molecular distribution of this alkali-soluble lignin fraction is depicted in FIG. 3, t=0.

Example 3: Enzymatic Oxidation of Lignin in a Batch Reaction

Alkali-soluble lignin prepared as described above was dissolved in 750 ml water to the final concentration of 25 g/L to obtain a lignin solution. The reaction was run in 1 L twin-pot bioreactor (BIOSTAT® B plus twin from Sartorius Stedim Biotech). The reactor with lignin solution was equilibrated to 50 C, and pH 10.5 with aeration at a rate of 0.16 l/min. After that, the enzyme was added to an amount of 800 nkatal/gram of lignin (~50 U/gram of lignin). The reaction was continued for 5 hours (h) with constant aeration at a rate of 0.16 l/min. Dissolved oxygen level was maintained at a constant level from the time of enzyme addition and the pH was controlled with NaOH to remain at 10.5 throughout the reaction. Samples after 1 h and after 5 h were collected and analyzed by size exclusion chromatography (FIG. 3, t=1 h and t=5 h). All samples were diluted 1:49 with 0.1M NaOH for HPLC injection.

Example 4: Enzymatic Oxidation of Lignin with Continuous Ultrafiltration

Figure 4:
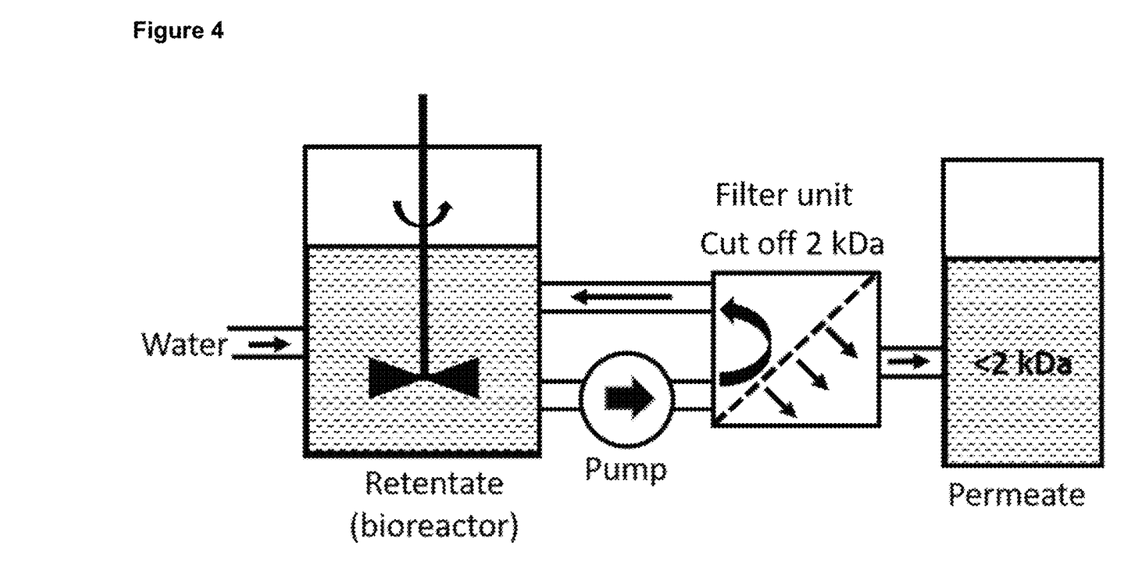
FIG. 4: Schematic representation of a process according to the invention.
Figure 5:
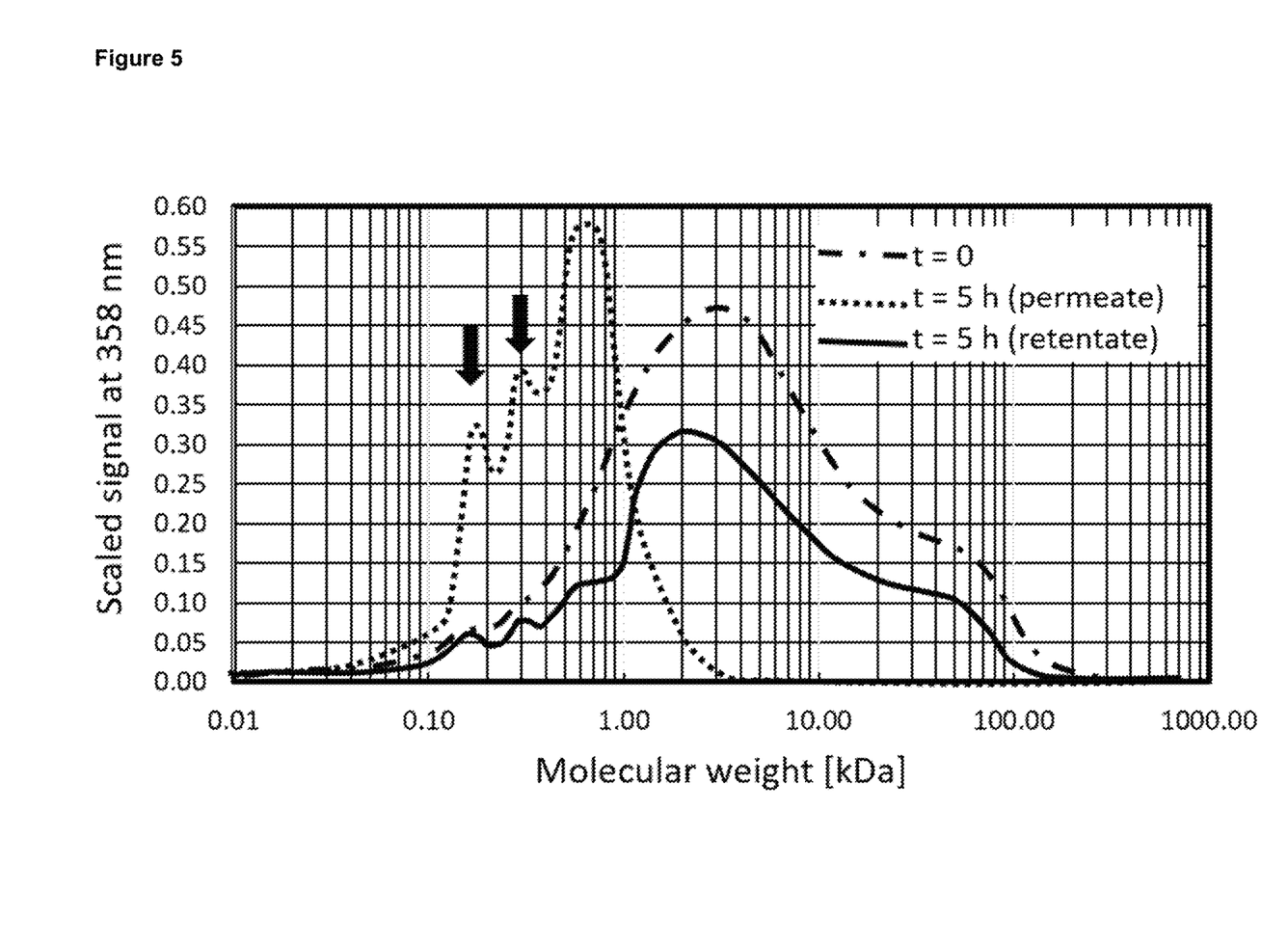
FIG. 5: Molecular weight distribution of lignin molecules determined by size exclusion chromatography in a process according to the invention wherein low molecular weight lignin is selectively removed from the reaction mixture during the reaction. Samples were taken after reaction time t. Dash-dotted line: starting point t=0; solid line: retentate at t=5 h; dotted line: permeate at t=5 h. Arrows show approximate molecular weights of monomer and dimer lignin units.

Alkali-soluble lignin prepared as described above was dissolved in 750 ml water to the final concentration of 25 g/L to obtain a lignin solution. The reaction was run in 1 L twin-pot bioreactor (BIOSTAT® B plus twin from Sartorius Stedim Biotech). The reactor with lignin solution was equilibrated to 50 C, and pH 10.5 with aeration at a rate of 0.16 l/min. After that, the enzyme was added to an amount of 800 nkatal/gram of lignin (~50 U/gram of lignin). The reaction was continued for 1 h in a batch mode with constant aeration at a rate of 0.16 l/min. Dissolved oxygen level was maintained at a constant level from the time of enzyme addition and the pH was controlled with NaOH to remain at 10.5 throughout the reaction. After one hour, the reaction was switched to continuous filtration mode (FIG. 4) for 4 hours (thus total reaction time was 5 h). The reaction mixture was continuously circulated through a tangential flow membrane unit Vivaflow 200 (Sartorius) with polyethersulfone membranes with 2 kDa cut-off value. The filtration unit was used according to the manufacturer's protocol (2.5 bar pressure, 200-400 ml/min retentate flow/module). While the reaction was circulated through the filtration unit, the reaction conditions (pH and temperature) were maintained in the reactor and the reaction mixture was replenished with water to keep the volume in the reactor constant. The permeate accumulation rate was approximately 2 L/h, thus the whole reaction volume was replaced in approximately 20 min. Samples were analysed by HPLC.

To normalize the volumes of different fractions (starting material, retentate and permeate) for HPLC analysis, retentate sample was used undiluted, permeate sample was diluted with water 1:0.1, starting material sample was diluted with water 1:10.6.

All three samples were further diluted 1:4 with 0.1M NaOH for HPLC injection.

Example 5: Size exclusion HPLC

Size exclusion chromatography for lignin samples and molecular weight standards was performed using HPLC chromatographer 120 Compact LC with UV detector (Agilent Technologies), equipped with size exclusion column MCX 1000 Angstrom 5 µm, 8×300 mm and with pre-column MCX 5 µm, 8×50 mm (Polymer Standards Service). Isocratic mode with 0.1M NaOH eluent flow 0.5 ml/min at room temperature was used; run time was 40 min. The detection was performed at 358 nm. Molecular mass standards (polystyrene sulfonate sodium salt standards Mp=~ 0.9 to ~65 kDa, Polymer Standards Service) were monitored at 254 nm. Data were acquired with EzChrom Elite Compact software.

Primary HPLC traces acquired with Agilent EZChrom Elite software were transferred to tailor-made MS Excel spreadsheets for further processing. Signal versus retention time graphs were produced from 1 Hz time series to depict the chromatography traces.

Polystyreen sulfonate Molecular mass standards (Polymer Standards Service), ranging in mass at peak maximum from MW=~ 900 to ~65000, and syringaldehyde (MW 182) were used for calibration of molecular weights.

Based on HPLC profiles, the weight average molecular weight (Mw), were calculated for lignin fractions.

The Mw was calculated using the equation:

$$Mw = \frac{\sum (WiMi)}{w} = \frac{\sum (HiMi)}{\sum Hi}$$

Wherein W is the total weight of polymers, Wi is the weight of i-th polymer, Mi is the molecular weight of the i-th elution time and Hi is the height of i-th elution time.

REFERENCES

1) Martone et al., Current Biology. 19 (2): 169-75 (2009)
2) Lebo et al., Encyclopedia of Chemical Technology. John Wiley & Sons, Inc. ISBN 0-471-23896-1.
3) Wardrop; Aust. J. Botany. 17 (2): 229-240 (1969).
4) Freudenberg & Nash (eds) Constitution and Biosynthesis of Lignin. Berlin: Springer-Verlag (1968).
5) Boerjan et al., "Lignin biosynthesis". Annu. Rev. Plant Biol. 54 (1): 519-549 (2003).
6) Kuroda et al., J Agric Food Chem. 49 (4): 1840-1847 (2001).
7) Ralph et al. Phytochemistry 57 (6): 993-1003 (2001).
8) Munk et al., Biotechnology Advances 33:13-24 (2015).
9) Hamalainen et al., Front. Bioeng. Biotechnol, 6:20 doi: 10.3389/fbioe.2018.00020 (2018).
10) Glazer and Nikaido, (1995). Microbial Biotechnology: fundamentals of applied microbiology. San Francisco: W. H. Freeman, p. 340. ISBN 0-71672608-4.

---

The invention claimed is:

1. A method for producing lignin with a low molecular weight, the method comprising
    contacting high molecular weight lignin with an alkaline laccase at alkaline pH in a reaction vessel, and
    selectively removing lignin with a molecular weight below 2 kDa from the reaction vessel during the contacting.

2. Method according to claim 1 which is a fed batch process or a continuous process.

3. Method according to claim 1 wherein the laccase is a bacterial laccase.

4. Method according to claim 3 wherein the laccase is a CotA laccase.

5. Method according to claim 1 wherein the laccase comprises an amino acid sequence according to SEQ ID NO: 1 or an amino acid sequence at least 90% identical to SEQ ID NO: 1.

6. Method according to claim 1 wherein the alkaline pH is between 8 and 14.

7. The method according to claim 1, wherein the laccase is a *Bacillus* spore coat laccase.

8. The method according to claim 1, wherein the alkaline pH is between 8 and 13.

9. The method according to claim 1, wherein the alkaline pH is between 8 and 12.

10. The method according to claim 1, wherein the alkaline pH is between 9 and 12.

11. The method according to claim 1, wherein the alkaline pH is between 9 and 11.

* * * * *

SEQUENCE LISTING

<160> NUMBER OF SEQ ID NOS: 1

<210> SEQ ID NO 1
<211> LENGTH: 512
<212> TYPE: PRT
<213> ORGANISM: Bacillus wakoensis

<400> SEQUENCE: 1

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile

```
            20                  25                  30
Gln Glu Phe Lys Lys Lys Leu His Arg Asp Leu Pro Pro Thr Thr Leu
         35                  40                  45
Trp Gly Tyr Asn Ala Gln Phe Pro Gly Pro Thr Ile Glu Ala Asn Ser
         50                  55                  60
Asn Glu Pro Val Glu Val Lys Trp Ile Asn Glu Leu Pro Asn Lys His
 65                  70                  75                  80
Phe Leu Pro Val Asp Trp Ser Ile Met Asn Lys Asp Leu Pro Glu Val
                 85                  90                  95
Arg His Val Thr His Leu His Gly Gly Arg Thr Pro Trp Val Ser Asp
                100                 105                 110
Gly Tyr Pro Glu Ala Trp Tyr Thr Lys Asp Tyr Lys Glu Val Gly Ser
                115                 120                 125
Phe Phe Lys Glu Glu Val Tyr Arg Tyr Leu Asn Glu Gln Arg Ala Met
                130                 135                 140
Met Leu Trp Tyr His Asp His Thr Met Gly Ile Thr Arg Leu Asn Asn
145                 150                 155                 160
Tyr Ala Gly Leu Ala Gly Ala Tyr Ile Ile Arg Asp Lys His Glu Lys
                165                 170                 175
Ser Leu Asn Leu Pro Glu Gly Glu Tyr Glu Val Pro Leu Ile Ile Gln
                180                 185                 190
Asp Arg Thr Phe Asn Glu Asp Gly Ser Leu Phe Tyr Pro Thr Gly Pro
                195                 200                 205
Glu Asp Gly Gly Glu Asp Leu Pro Asn Pro Ser Ile Val Pro Ala Phe
                210                 215                 220
Leu Gly Asp Thr Val Leu Val Asn Gly Lys Val Trp Pro Tyr Leu Glu
225                 230                 235                 240
Val Glu Pro Arg Lys Tyr Arg Phe Arg Ile Leu Asn Gly Ser Asn Thr
                245                 250                 255
Arg Ser Tyr Gln Leu His Leu Asp Ser Asn Gln Glu Val Tyr Gln Ile
                260                 265                 270
Gly Ser Asp Gly Gly Leu Leu Glu Lys Pro Val Gln Met Asn Lys Ile
                275                 280                 285
Pro Ile Glu Ser Ser Glu Arg Ile Asp Val Ile Ile Asp Phe Ser Gln
                290                 295                 300
Cys Asp Gly Asp Glu Ile Val Leu Lys Asn Asp Leu Gly Pro Asp Ala
305                 310                 315                 320
Asp Ala Glu Asp Glu Thr Asn Glu Ile Met Lys Phe Lys Val Ser Lys
                325                 330                 335
Pro Leu Lys Glu Lys Asp Thr Ser Val Ile Pro Lys Arg Leu Ser Thr
                340                 345                 350
Ile Arg Ser Leu Arg Asn Asn Lys Ile Ser Thr His Arg Asn Leu Lys
                355                 360                 365
Leu Val Gly Ser Thr Asp Phe Gly Arg Pro Leu Leu Leu Asn
                370                 375                 380
Asn Lys Lys Trp Ala Asp Pro Thr Thr Glu Lys Pro Lys Val Gly Asp
385                 390                 395                 400
Thr Glu Val Trp Ser Phe Ile Asn Thr Thr Asp Phe Ala His Pro Met
                405                 410                 415
His Ile His Leu Ile His Phe Gln Val Leu Asp Arg Gln Pro Phe Asp
                420                 425                 430
Leu Glu Arg Tyr Asn His Asp Gly Thr Ile Ile Tyr Thr Gly Pro Pro
                435                 440                 445
```

-continued

```
Arg Ala Pro Glu Pro Asn Glu Arg Gly Trp Lys Asp Thr Val Ser Ala
    450             455             460

Pro Ala Gly Gln Ile Thr Arg Val Ile Gly Thr Phe Ala Pro Tyr Thr
465             470             475             480

Gly Asn Tyr Val Trp His Cys His Ile Leu Glu His Glu Asp His Asp
            485             490             495

Met Met Arg Pro Met Lys Val Ile Asp Pro Lys Gln Arg Lys Asp Lys
            500             505             510
```